United States Patent [19]

Egle

[11] Patent Number: 4,552,102
[45] Date of Patent: Nov. 12, 1985

[54] SYSTEM FOR IMPROVING THE STARTING OF DIESEL ENGINES IN COLD WEATHER

[76] Inventor: Edward J. Egle, 293 S. Circle Dr., Palatine, Ill. 60067

[21] Appl. No.: 661,262

[22] Filed: Oct. 15, 1984

Related U.S. Application Data

[60] Continuation-in-part of Ser. No. 403,861, Jul. 30, 1982, abandoned, which is a division of Ser. No. 260,179, May 4, 1981, abandoned.

[51] Int. Cl.⁴ .............................................. F02N 17/00
[52] U.S. Cl. ........................ 123/179 H; 123/179 B; 123/179 BG; 123/145 A; 123/640; 219/486
[58] Field of Search ........ 123/179 H, 179 B, 179 BG, 123/145 A, 640, 641; 219/486, 505

[56] References Cited

U.S. PATENT DOCUMENTS

| 1,172,698 | 2/1916 | Fynn et al. | 123/640 |
|---|---|---|---|
| 1,236,941 | 8/1917 | Huff | 123/640 |
| 1,258,785 | 3/1918 | Kettering et al. | 123/641 |
| 1,435,392 | 11/1922 | Heiser | 123/145 A |
| 1,590,892 | 6/1926 | Heany | 123/145 A |
| 1,609,688 | 12/1926 | Briggs | 123/145 A |
| 4,137,885 | 2/1979 | Van Ostrom | 123/179 H |
| 4,258,678 | 3/1981 | Abe | 123/179 H |
| 4,285,307 | 8/1981 | Steinke | 123/179 H |
| 4,348,583 | 9/1982 | Bube et al. | 123/179 H |
| 4,351,291 | 9/1982 | Mahaney | 123/145 A |
| 4,399,781 | 8/1983 | Tsukasaki | 123/179 H |

FOREIGN PATENT DOCUMENTS

| 0883277 | 6/1943 | Italy | 123/640 |
|---|---|---|---|
| 0047040 | 4/1979 | Japan | 123/179 H |
| 0461193 | 2/1937 | United Kingdom | 219/486 |

*Primary Examiner*—Parshotam S. Lall

[57] ABSTRACT

A system for improving the starting of indirect and direct injection diesel engines in cold weather, including glowplugs powered by a source of electrical potential for heating the diesel fuel and circuitry for controlling the operation of the glowplugs.

7 Claims, 6 Drawing Figures

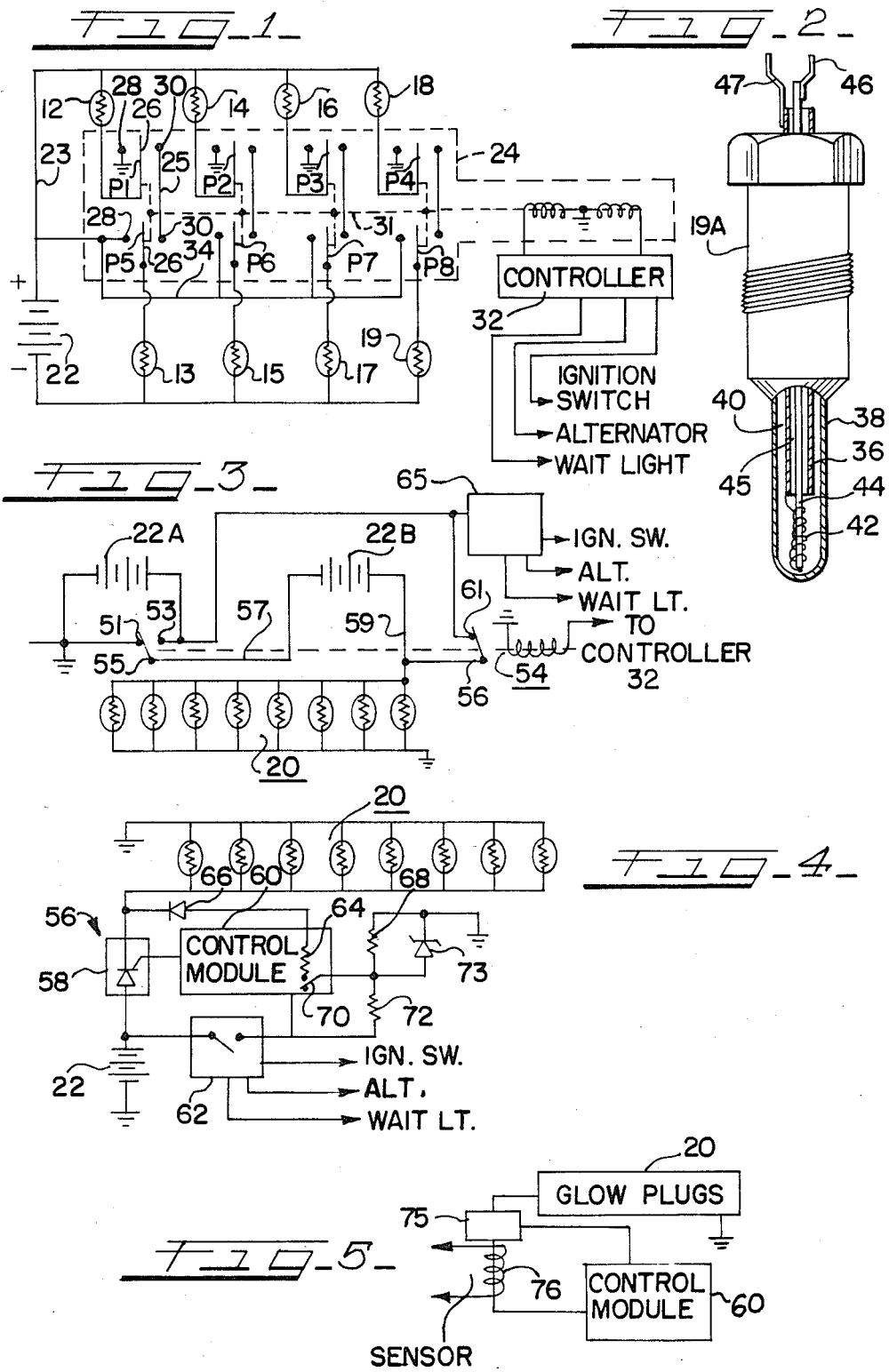

SYSTEM FOR IMPROVING THE STARTING OF DIESEL ENGINES IN COLD WEATHER

This application is a continuation-in-part, of application Ser. No. 403,861, filed July 30, 1982, now abandoned, which is a division of 06/260,179, filed 05/04/81, now abandoned.

DESCRIPTION

1. Technical Field

The present invention relates generally to a system for facilitating the starting of indirect and direct injection diesel engines in cold weather.

1. Background Prior Art

Successful cold starting of indirect and direct injection diesel engines requires the diesel fuel to be heated above the flash temperature. This is normally accomplished by glowplugs, which are, in effect, high impedance electrical resistance heaters energized by the associated battery power source. Glowplug systems attempt to make the starting of diesel engines as quick, easy and convenient as the starting of gasoline spark-ignited engines.

An early type of glowplug system operated with twelve (12) volt glowplugs, using a twelve (12) volt supply, and required a sixty (60) second preglow period before the engine could be cranked. The term "preglow" refers to the heating period, measured from the time the glowplug is initially energized to the time when the engine can be cranked; it is, therefore, a waiting period for the user before the engine can be cranked. Present-day light-duty diesel engine users will not tolerate a sixty (60) second wait period before cranking the engine.

Accordingly, various prior art systems for providing faster starts for indirect and direct injection light-duty diesel engines have been developed. However, presently available glowplug systems continue to have problems, particularly in cold weather starting. It will be appreciated that the higher and and more consistent the glowplug operating temperature, the better the starting capabilities of the system, especially in sub-zero weather.

Present glowplug systems represent a compromise between a long preglow period to obtain a high consistent temperature and a shorter preglow period with fluctuating cranking temperatures, providing less than optimum starting characteristics in sub-zero weather. One starting glowplug system for disesel engines consists of flowplugs which have a continuous voltage supplied thereto and a controller to correct for required warmup time, based on engine temperature. This system includes glowplugs rated for continuous twelve (12) volt operation with a twelve (12) volt power supply.

Another such fast-start prior art system provides rapid warmup time by utilizing six (6) volt glowplugs instead of twelve (12) volt glowplugs, and by utilizing a twelve (12) volt power supply and a controller for a specific duty cycle operating after the preglow period. During the cranking and afterglow periods, approximately twenty percent (20%) duty cycle is applied to the glowplugs. This duty cycle attempts to sustain the temperature of the glowplug by using an approximately one (1) second ON period and sufficiently long OFF period to prevent glowplug overheating. The applied duty cycle provides less than optimum performance by allowing the glowplug to operate on a cooling cycle 80% of the time. Hence, the total heat provided is less than optimum, and results in lower average glowplug operating temperature.

Most glowplug systems also provide for a sixty (60) second "afterglow" period, which is the period measured from the time after the engine is started to the time when the power to the glowplug is removed. An afterglow period is provided to improve idle status operation and to eliminate white smoke.

SUMMARY OF THE INVENTION

This invention provides an improved system, apparatus and method of utilizing standard and modified glowplugs for enhancing the cold starting capability of indirect and direct injection diesel engines.

This invention provides such a system, apparatus and method which obtains a fast preglow warmup and maintains maximum optimum operating temperature and eliminates the cyclic temperatures encountered in prior art on-off type duty cycles. This inventive system also applies a continuous lower voltage and more uniform constant voltage across the glowplug after the initial preglow warmup.

BRIEF DESCRIPTION OF SEVERAL VIEWS OF DRAWINGS

The foregoing features and advantages of the present invention will be apparent from the following more particular description of the invention. The accompanying drawings, listed herein below, are useful in explaining the invention wherein:

FIG. 1 is a schematic diagram of one embodiment of the inventive system;

FIG. 2 is a plan view of a modified glowplug in accordance with the invention;

FIG. 3 is a schematic diagram of a second embodiment of the invention;

FIG. 4 is a schematic diagram of another embodiment of the invention;

FIG. 5 is a schematic diagram of another embodiment of the invention;

DETAILED DESCRIPTION

Figure 6:
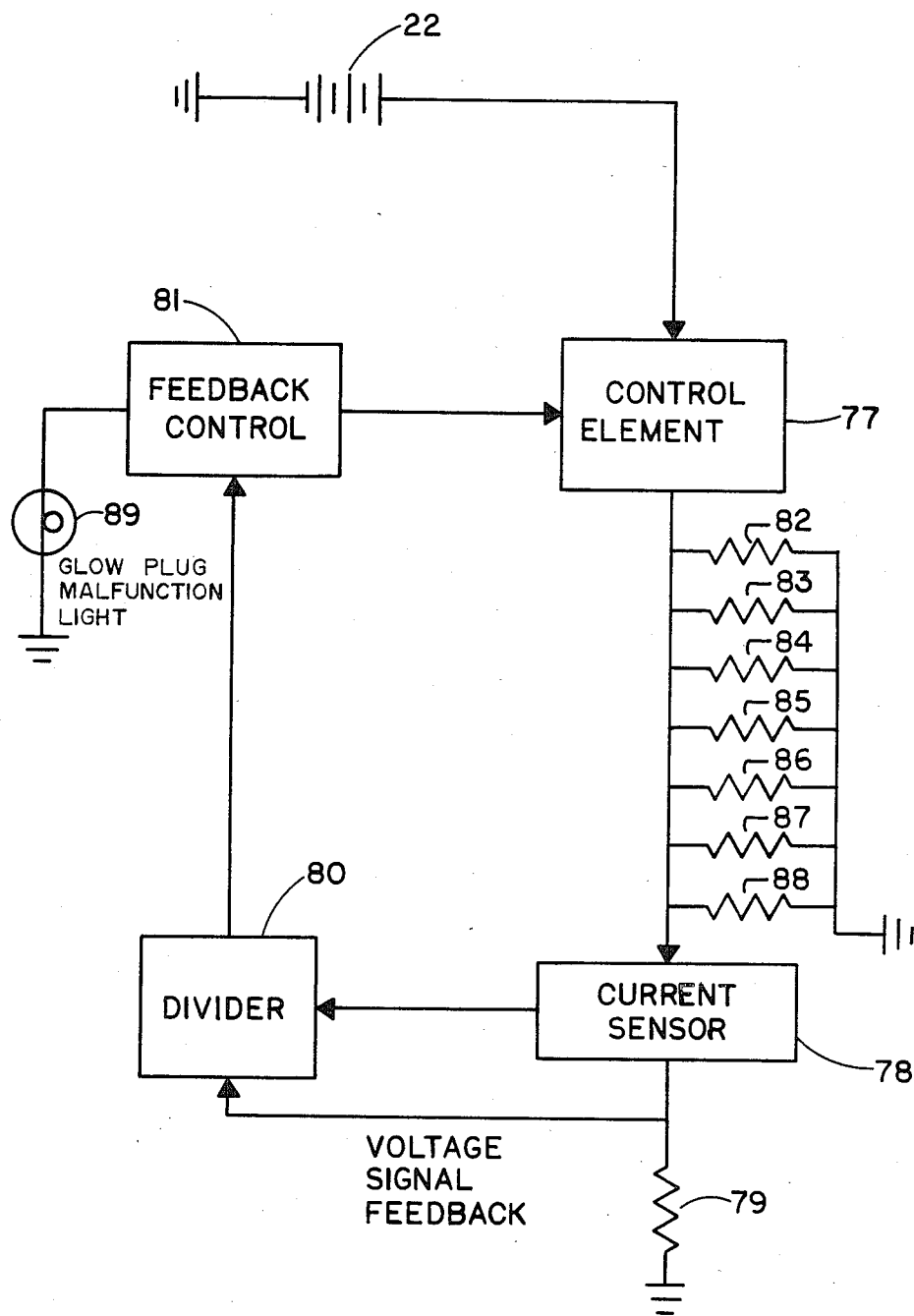
FIG. 6 is a schematic diagram of yet another embodiment of the invention.

The circult of FIG. 1 is a typical schematic diagram for an eight (8) cylinder diesel engine. Suitable modifications for any diesel engine of one (1) or more cylinders may be made to the inventive system. FIG. 1 shows eight six (6) volt glowplugs, numbered 12–19. Glowplugs labeled 13, 15, 17 and 19 are of a standard type, while glowplugs 12, 14, 16 and 18 are of a modified construction, as shown in FIG. 2, to be described hereinbelow. Glowplugs 12–19 are connected through the contacts of relay 24 to be heated by a direct connection to a twelve (12) volt battery 22. Relay 24 comprises an eight (8) pole triple throw relay 24, with a neutral position, of known design. In FIG. 1, the poles of the relays 24 are labeled P1–P2. The movable contacts of relay 24 are generally labeled 26, and are mechanically ganged together to be controllably operated by a controller 32. Controller 32 may be of any suitable known type which is responsive to engine temperature. In certain instances, a timing device may be used in lieu of the controller 32.

The movable contacts 26 of each of relay poles P1, P2, P3 and P4 are connected to the glowplugs 12, 14, 16 and 18, respectively. A stationary contact, generally labeled 28, of each of the relay poles P1, P2, P3 and P4 is connected to ground. The other stationary contact, generally labeled 30, of poles P1, P2, P3 and P4 is connected, respectively, to a stationary contact 30 of poles P5, P6, P7 and P8. The movable contacts 26 of each of relay poles P5, P6, P7 and P8 are connected to glowplugs 13, 15, 17 and 19, respectively. One stationary contact of each of poles P5, P6, P7 and P8 is connected to the battery 22 through lead 34.

Note that the glowplugs 12, 14, 16 and 18 are not directly grounded. Reference will hereinafter be made to FIG. 2 to explain the modification of the glowplug structure so that it may be utilized in the ungrounded circuit configuration of FIG. 1.

The circuit of FIG. 1 operates to heat up the six (6) volt glowplugs 12-19 by direct connection across the twelve (12) volt battery 22 for up to twelve (12) seconds, dependent on engine temperatures. In this operating condition, the controller 32 causes the linkage 31 to actuate the movable contacts 26 of each of the relay 24 pole pieces P1-P8 to make electrical contacts with the respective stationary contacts 28.

During the zero to twelve (12) second preglow period, the circuit path for glowplug 12 may be traced from the positive terminal of battery 22, through lead 23, glowplug 12, movable contact 26 of pole P1, to stationary contact 28 and ground reference. A similar circuit path as for glowplug 12 may be traced for each of glowplugs 14, 16 and 18.

The circuit path for glowplug 13 may be traced from the positive terminal of battery 22, through stationary contact 28 of pole P5, movable contact 26 of pole P5 and glowplug 13, to the negative terminal of battery 22. A similar circuit path as for glowplug 13 may be traced for each of glowplugs 15, 17 and 19.

After the initial zero to twelve (12) second preglow heating period, the controller 32 causes the movable contacts 26 of each of pole pieces P1-P8 to make contact with the respective stationary contacts 30. The glowplugs 12-19 will thus be connected in series, in pairs, across the battery 22. An electrical circuit path may be traced from the positive terminal of battery 22, through lead 23, through glowplug 12, movable contact 26 of pole P1, stationary contact 30, lead 25, stationary contact 30 of pole P5, movable contact 26 of pole P5, glowplug 13, to the negative terminal of battery 22. Similar circuit paths are traceable for the glowplugs 14 and 15, 16 and 17, and 18 and 19.

The controller 32 electrically couples to the engine ignition switch, the alternator and the wait light, as indicated in FIG. 1.

The foregoing operation enables a fast heating of the glowplugs 12-19 during the zero to twelve (12) second preglow period by providing twelve (12) volts to be impressed across each glowplug, and then will enable the glowplugs to maintain a higher, more constant operating temperature to improve the cold weather starting capability by providing a constant six (6) volts to be impressed across each glowplug. Note that a zero preglow period would be required to restart a hot engine.

FIG. 2 shows a glowplug 19A, corresponding to the glowplugs 12, 14, 16 and 18 of FIG. 1. The glowplug 19A is a modification of a standard glowplug such as shown in U.S. Pat. No. 4, 196,712 and U.S. Pat. No. 1,609,688 (incorporated herein by reference) in that a conductive tube 36, coaxially mounted in glowplug housing 38, is electrically insulated from housing 38 by insulation 40 which may be a material or air insulation, as is well-known. The heater coil 42 of the glowplug 19A has one end connected to a conductive rod 44, coaxially mounted in tube 36 and insulated therefrom by suitable insulation 45 along its length. The other end of coil 42 is connected to the tube 36. The outer end 46 of rod 44 provides one electrical input terminal; and the outer end 47 of tube 36 provides the other electrical input terminal. Note that the tube 36, heater coil 42 and rod 44 are not grounded to the glowplug housing 19A.

Presently, it is common practice to provide two twelve (12) volt batteries to provide adequate starting power for diesel engines. A second embodiment of the invention makes use of this factor in its glowplug heating operation. As shown in FIG. 3, this embodiment utilizes twelve (12) volt, long preglow warmup, glowplugs indicated generally as 20, and energizes the glowplugs by the two twelve (12) volt batteries 22A and 22B which are connectable in series by the contacts of relay 54. The circuit of FIG. 3 utilizes relay 54, which is controlled by controller 32, to selectively connect the batteries through movable contact 55 of relay 54 to provide 24 volts to operate the glowplugs 20. The circuit path for connecting the batteries 22A and 22B in series across the glowplugs 20 may be traced from battery 22A, through stationary contact 53, movable contact 55, lead 57, battery 22B and lead 59, to the glowplugs 20 and to ground reference. Movable contact 56 of relay 54 engages the stationary contact 61 to effectively shunt the remaining electrical system during this period so that only only the glowplugs 20 are energized. Controller 32 then energizes relay 54 to disconnect battery 22A and connect only battery 22B in the circuit to provide an operative twelve (12) volt source. The circuit path for this latter operation may be traced from battery 22B, through lead 59, glowplugs 20, ground reference, stationary contact 51, movable contact 55, lead 57, and back to the battery 22B. A suitable electronic interface 65 connects the circuit of FIG. 3 to the ignition switch, the alternator and the wait light, as indicated.

FIG. 4 shows another embodiment of the invention for controlling the flow of current to the glowplugs and for maintaining a constant temperature at the glowplugs. The electronic circuit 56 of FIG. 5 includes a gate-controlled SCR (silicon-controlled rectifier) 58, of a type known in the art. The anode of SCR 58 is connected to a battery 22; the gate electrode of SCR 58 is coupled to a control unit or module 60, such as a suitable microprocessor unit; and the cathode of SCR 58 is connected to the six (6) volt glowplugs 20.

Switch module 62, indicates as a mechanical switch for simplicity in the drawing, comprises a suitable electronic switch, and is connected to battery 22 to provide power to the control module 60 for a period as long as ten (10) to twelve (12) seconds prior to starting the engine and for one (1) minute after the engine has started. Switch 62 is activated by the ignition switch, as indicated in FIG. 4, to provide the preglow and afterflow time periods. The control module includes a resistor 64 connected in series with a diode 66 to the cathode of SCR 58 and, thus, also to the glowplugs 20. An electronic switch 70, indicated as a mechanical switch for simplicity, in the control module 60 is intermittently closed and opened.

Control module 60 controls the operation of SCR 58, and senses the resistance of the glowplugs 20 on an intermittent basis to constantly update the value of the resistance of the glowplug 20. Note that the resistance of the glowplugs 20 is a direct indication of the temperature of the glowplug element. Electronically-operated switch 70 selectively switches the SCR 58 to momentarily stop current flow. During this power-off part of the SCR cycle, the resistance of the glowplugs 20 is sensed and updates the operating parameters of the control module 60, in accordance with a preset program. The voltage drop across the resistor 64 will be an indication of the current flow in this circuit, and also a direct indication of the resistance; hence, of the temperature of the glowplugs 20. When module 60 senses the required voltage drop across resistor 64, the control module 60 limits the current flow through the SCR 58 to maintain the optimum glowplug 20 operating temperature.

The control module 60 will thus provide maximum current flow through the six (6) volt glowplugs until the operating temperature is obtained. The switch module 62, in combination with module 60, also provides an indication, such as by the wait light, when the glowplugs reach operating temperature so that the operator can begin cranking the engine. Module 60 then reduces the current flow through the glowplugs 20 in steps to maintain optimum glowplug operating temperature.

The resistor 64 provides a constant value resistance, that is, there is no change in its resistance with a change in temperature. A constant voltage supply is obtained by use of a resistor 68 and a Zener diode 73, connected in parallel to resistor 68. Note that a suitable voltage regulator IC (integrated chip) may be used in lieu of the Zener diode 73. Resistor 72 compensates for the drop in battery voltage when the engine is cranked.

During the cranking period, the glowplugs will operate continuously in the lower voltage mode. After the engine starts, the glowplug controller 32 modulates the power delivered to the glowplug to sustain the application of power in a lower voltage mode to the glowplugs 20 for a preselected period, determined such as by an electronic module 62, to provide an "afterglow" period. Switch module 62 connects to the engine ignition switch, the alternator and the wait light, as indicated.

As shown in FIG. 5, in another embodiment of the invention, a sensor 76 of any suitable type, such as a magnetic field pick-up sensor or a current flow sensor, is utilized in lieu of the constant value resistor 64. A current interrupter 75, of suitable known design and indicated as a mechanical switch, provides the necessary current pulsing to operate the magnetic pick-up 74. Sensor 76 determines the current flow through the glowplugs during the off period of the unit 75. The current flow would be inversely proportional to the resistance (temperature) of the glowplugs 20. The current interrupter may be a silicon-controlled rectifier (SCR), as in FIG. 4; and sensor 76 can control this SCR similarly as described above with reference to FIG. 4. Otherwise, the system of FIG. 5 is similar to the circuit of FIG. 4.

As shown in FIG. 6 in a schematic drawing in another embodiment of the invention, current flows from Battery 22 through control element 77 through glowplugs i.e. 82–88 (one less than number of diesel cylinders) and through current sensor 78 through single glowplug 79 to ground.

Control element 77 supplies a pulse width modulated power or control of current operating at an optimized frequency such as 50 to 60 cycles through glowplugs 82 to 88 and to current sensor 78 to glowplug 79.

Current sensor 78 which can be a non contact method using a transformer or Hall effect IC senses the current flow through glowplug 79. Current sensor 78 sends a proportionate signal of the pulse width modulated cycle.

Signal from current sensor 78 is fed into divider 80 along with the voltage signal applied to glowplug 79. The divider 80 sends a proportional signal to the feedback control 81 which then controls control element 77 determining the width of the duty cycle applied. Divider 80 calculates the resistance of the glowplug 79 using Ohms law $R = E/I$ with E being the average voltage applied across the glowplug 79 and I being the average current flowing through the glowplug 79. This resultant resistance is a direct indication of the temperature of the glowplug 79.

Only one glowplug is used for resistance calculations as it will provide a safe condition in case of a failure of that glowplug.

Ignition switch, alternator connections and wait light would also apply to this circuit. These glowplugs 79 and 82 through 88 would be low voltage type glow plugs as compared to source voltage. This system would provide a fast preheat of the glowplugs and maintain optimum non fluctuating temperature during the cranking and cold engine operation periods. 89 is a warning light to indicate any malfunction such as open circuit or short of the glowplug 79.

The proposed new system components can be installed in lieu of existing systems at the time of manufacture. Also, a modification or retrofit kit can be supplied for easy and expeditious installation to replace or modify existing systems in operating engines.

A manual override switch may be provided in all five embodiments for use of either as a starting fluid in lieu of total disregard by operator for glowplug system in case of system failure. Present common operator practice in the field is to spray ether in the engine for cold weather starting by those who know how to handle it. This requires cut-off of the glowplug system.

While the invention has been particularly shown and described with reference to a preferred embodiment thereof, it will be understood by those skilled in the art that various changes in form and details may be made therein without departing from the spirit and scope of the invention.

I claim:

1. A system utilizing glowplugs electrically connectable to a source of potential for heating the fuel provided to an associated diesel engine for facilitating the starting of the engine, particularly in cold weather, and responsive to engine and atmospheric conditions, comprising, in combination:
   (a) a first group of glowplugs;
   (b) a second group of glowplugs;
   (c) selectively actuatable switching means having a plurality of movable contacts and at least first and second stationary contacts;
   (d) controller responsive to engine and atmospheric conditions as a means for actuating said movable contacts to selectively contact said first and second stationary contacts;
   (e) said switch means in a first condition connecting each of said glowplugs in said first and second groups to receive the full voltage of said source of potential thereacross, whereby said glowplugs are heated to a high temperature at a relatively fast rate; and (f) said switch means in a second condition connecting a glowplug of said first group, respectively in series with a glowplug of said second group to thereby reduce the voltage from said source of potential for maintaining the temperature of the glowplugs at a preselected level.

2. A system as in claim 1, wherein said electronic switching means comprises a relay having a plurality of poles, each pole having a movable contact, first and second stationary contacts and a neutral position.

3. A system as in claim 1, wherein said controller means comprises variable timing means according to environmental conditions.

4. A system utilizing glowplugs electrically connectable to sources of potential for heating the fuel provided to an associated diesel engine for facilitating the starting of the engine, particularly in cold weather, comprising, in combination:
   (a) a plurality of glowplugs;
   (b) relay means having movable contacts and stationary contacts;
   (c) controller means for actuating said movable contacts to selectively contact said stationary contacts;
   (d) first and second battery means;
   (e) first circuit means for connecting said first and second batteries in series through selected ones of contacts to provide a relatively high voltage to energize and heat said glowplugs relatively quickly; and
   (f) second circuit means for connecting both of said batteries in parallel through others of said contacts to provide a constant lower voltage to said glowplugs.

5. A system utilizing glowplugs electronically connectable to a source of potential for heating the fuel provided to an associated diesel engine for facilitating the starting of the engine, particularly in cold weather, comprising, in combination:
   (a) a plurality of glowplugs having a repeatable temperature versus resistance characteristics;
   (b) electronic switch means for connecting said source of potential to energize and heat said glowplugs;
   (c) a resistance comparator and control module including a stable voltage reference, and sensing means for sensing the resistance of the glowplugs on an intermittent basis and for updating the value of resistance whereby the temperature of said glowplugs is monitored;
   (d) said control module actuating said switch means for providing intermittent current flow to said glowplugs to controllably cause said glowplugs to reach and maintain a preselected temperature; and
   (e) said electronic switch may be a gate controlled SCR or any other equivalent performing device which will modulate the current flow and hence applied voltage to the glowplugs.

6. A system as in claim 5 wherein said sensing means comprises a magnetic sensing means for sensing the flow of current through said plugs.

7. A system utilizing plowplugs electronically connectable to a source of potential for heating the fuel provided to an associated diesel engine for facilitating the starting of the engine, particularly in cold weather, comprising, in combination:
   (a) a plurality of glowplugs having a repeatable temperature versus resistance characteristics;
   (b) electronic switch means for connecting said source of potential to energize and heat said glowplugs;
   (c) an electronic regulating device with closed loop feedback for computing the actual resistance (actual temperature) of the glowplug by sensing actual current and voltage applied; and
   (d) said electronic regulating device with closed loop feedback actuating said switch.

* * * * *